United States Patent
Lee et al.

(10) Patent No.: US 6,377,653 B1
(45) Date of Patent: Apr. 23, 2002

(54) METHOD FOR CALIBRATING TRABECULAR INDEX USING SAWTOOTH-SHAPED RACK

(75) Inventors: Sooyeul Lee; Hyeon-Bong Pyo; Seunghwan Kim; Seon Hee Park, all of Taejon (KR)

(73) Assignee: Electronics and Telecommunications Research Institute, Taejon (KR)

(*) Notice: Subject to any disclaimer, the term of this patent is extended or adjusted under 35 U.S.C. 154(b) by 0 days.

(21) Appl. No.: 09/498,319

(22) Filed: Feb. 4, 2000

(30) Foreign Application Priority Data

Dec. 10, 1999 (KR) ........................................ 1999-56359

(51) Int. Cl.[7] .............................................. G01B 15/02
(52) U.S. Cl. ........................................... 378/54; 378/56
(58) Field of Search .............................. 378/57, 54, 56, 378/58, 162, 163, 165; 600/407, 562, 587, 593, 594

(56) References Cited

U.S. PATENT DOCUMENTS

| 5,247,934 A | | 9/1993 | Wehril et al. ............. 128/653.2 |
| 5,365,564 A | * | 11/1994 | Yashida et al. ............... 378/55 |
| 5,712,892 A | | 1/1998 | Weil et al. ..................... 378/54 |
| 5,852,647 A | * | 12/1998 | Schick et al. ................. 378/53 |
| 6,282,258 B1 | * | 8/2001 | Stein et al. .................... 378/54 |

OTHER PUBLICATIONS

Isaac Leichter et al. "Optical and Digital Processing of Radiographs for the Early Detection of Osteoporosis," SPIE, vol. 2390, pp. 102–109.

* cited by examiner

Primary Examiner—David P. Porta
(74) Attorney, Agent, or Firm—Seed IP Law Group, PLLC

(57) ABSTRACT

A method for calibrating a trabecular index with a sawtooth-shaped rack which corrects an error in the trabecular index due to the characteristics of an image input device or radiographic conditions of an x-ray image when a bone mineral density is measured by setting up the trabecular index with trabecular patterns of a simple x-ray image. The present invention includes a method for calibrating the trabecular index with a sawtooth-shaped rack, wherein bone mineral density is measured with the trabecular index calculated from an x-ray image and an error in the trabecular index is calibrated by a method of calibrating the trabecular index, the method includes the following steps. A first step is preparing an x-ray image by radiographing a bone and a sawtooth-shaped rack together. A second step is attaining trabecular indexes from the x-ray image of the rack and the bone. And, a third step is calibrating the trabecular index of the bone with the trabecular index of the rack.

5 Claims, 4 Drawing Sheets

METHOD FOR CALIBRATING TRABECULAR INDEX USING SAWTOOTH-SHAPED RACK

TECHNICAL FIELD

The present invention relates to a method for calibrating a trabecular index with a sawtooth-shaped rack that corrects an error in the trabecular index due to the characteristics of the image input device or radiographic conditions of an x-ray image when a bone mineral density is measured by setting up the trabecular index with trabecular patterns of a simple x-ray image.

BACKGROUND OF THE INVENTION

Osteoporosis is a wide spread medical condition that affects the middle-aged and older populations. Especially, the condition is prevalent in postmenopausal women. Osteoporosis is characterized by an abnormal loss in bone mineral content, which leads to a tendency toward non-traumatic bone fractures and to structural deformations of bones. However, effective therapy for osteoporosis has not been developed yet. Only a few methods for reducing the possibility of occurrence of osteoporosis through physical exercise or appropriate diets are known. Accordingly, it is very important to develop a simple and inexpensive method of measuring bone mineral density so that osteoporosis can be diagnosed and treated in the early stages of the disease, thereby preventing further deterioration.

A bone mineral density measurement has been a basic tool for diagnosing osteoporosis because osteoporosis is characterized by an abnormal loss of bone mineral content. Various methods have been developed to obtain a quantitative measurement of bone mineral density. The most widely used method for measuring bone mineral density is dual photon absorptiometry with either an x-ray or nuclear source. The precision of this method to measure bone mineral density is within a few percent.

Two other methods for quantitatively measuring bone mineral density are Computerized Tomography and a Magnetic Resonance Imaging which provide three-dimensional bone density assessment, and separate estimations of cortical and trabecular bone densities. However, the routine use of these densitometries is precluded by their high costs.

Mechanical strength of the whole bone is determined mainly by the dense cortical bone. However, many recent studies have indicated that the trabecular bone is also an important factor in determining mechanical strength of bone. Moreover, it is well known that the trabecular bone is absorbed more rapidly than cortical bone in the case of osteoporosis. This implies that the trabecular bone is more reflective of the stage of osteoporosis and that early stage intervention in osteoporosis is possible through an evaluation of changes in the trabecular bone.

In this sense, many investigators have studied the trabecular patterns appearing on conventional x-ray images. The Saville index and the Singh index are available as clinical tools for assessing changes in trabecular patterns of x-ray images. These indices assess the stage of osteoporosis using density, direction, etc. of trabecular patterns appearing on x-ray images of the lateral lumber spine and the upper part of the femur.

Computerized image processing applies various textural methods to quantify changes in trabecular patterns appearing on an x-ray image, such as gray level statistics, frequency domain analysis, and fractal dimension analysis. These methods are reported to be somewhat successful to predict the fracture risk of bone.

Recently, a new method of trabecular indexing has been developed to quantify the trabecular pattern changes appearing on a simple x-ray image. This trabecular index method analyzes trabecular patterns appearing on an x-ray image and uses the analysis for the measurement of bone mineral density of the corresponding bone.

Unfortunately, when a trabecular index method is applied to a real x-ray image, the trabecular index of the corresponding bone may vary in accordance with the characteristics of an x-ray film digitizer and the x-ray radiographic conditions.

In general, each hospital uses different x-ray radiographic conditions and ray film digitizers. Thus, when the above trabecular indexing method is used by respective hospitals, the effect due to the difference of x-ray radiographic conditions and x-ray film digitizers should be corrected.

SUMMARY OF THE INVENTION

Accordingly, the present invention is directed to a method for calibrating a trabecular index with a sawtooth-shaped rack that substantially obviates one or more of the problems due to limitations and disadvantages of the related art.

The object of the present invention is to provide a method for calibrating a trabecular index with a sawtooth-shaped rack that corrects an error in a trabecular index due to the characteristics of an image input device or radiographic conditions of an x-ray image when a bone mineral density is measured by setting up a trabecular index with the trabecular patterns of a simple x-ray image.

Another object of the present invention is to provide a recording means for storing a program to realize a method for correcting a trabecular index.

Additional features and advantages of the invention will be set forth in the description that follows and in part will be apparent from the description, or may be learned by practicing the invention. The objectives and other advantages of the invention will be realized and attained by the structure pointed out in the written description and claims hereof as well as the appended drawings.

To achieve these and other advantages in accordance with the purpose of the present invention, as embodied and broadly described, the present invention includes a method for calibrating a trabecular index with a sawtooth-shaped rack, wherein bone mineral density is measured with a trabecular index. This index is calculated from an x-ray image and an error in the trabecular index is calibrated by a method including the following steps. The first step is preparing an x-ray image by radiographing a bone and a sawtooth-shaped rack together. The second step is attaining trabecular indexes from the x-ray image of the rack and the bone. The third step is calibrating the trabecular index of the bone with the trabecular index of the rack.

Preferably, the sawtooth-shaped rack consists of a thick sawtooth part modeling upon a thick trabecular bone and a thin sawtooth part modeling upon a thin trabecular bone.

More preferably, the sawteeth of the thick and thin sawtooth parts have the same pitch length and height, wherein the thickness under the sawteeth of the thick sawtooth part is thicker than a thickness under the sawteeth of the thin sawtooth part.

Furthermore, it is preferable that a calibrated trabecular index value "aa" of the bone is attained by the following formula provided that a trabecular index value of the measured bone is "a", a trabecular index value of the thick sawtooth part is "b", a trabecular index value of the thin sawtooth part is "c", and the ideal reference trabecular index values of the two sawteeth are "bb" and "cc", respectively:

$$aa=(a-c)(bb-cc)/(b-c)+cc$$

In another aspect, the present invention includes a recording means for storing a program for realizing a method of calibrating a trabecular index, the program includes the following steps. The first step is preparing an x-ray image by radiographing a bone and a sawtooth-shaped rack together. The second step is attaining trabecular indexes from the x-ray image of the rack and the bone. And the third step is calibrating the trabecular index of the bone with the trabecular index of the rack, wherein the program is read by the computer.

It should be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the inventing and together with the description serve to explain the principle of the invention.

In the drawings.

DETAILED DESCRIPTION OF THE INVENTION

Reference will now be made in detail to the preferred embodiments of the present invention, examples of which are illustrated in the accompanying drawings.

In advance of a method for calibrating a trabecular index of the present invention, a method of establishing a trabecular index with a trabecular pattern on a simple x-ray image, which is used for the present invention, will be explained.

Figure 1:
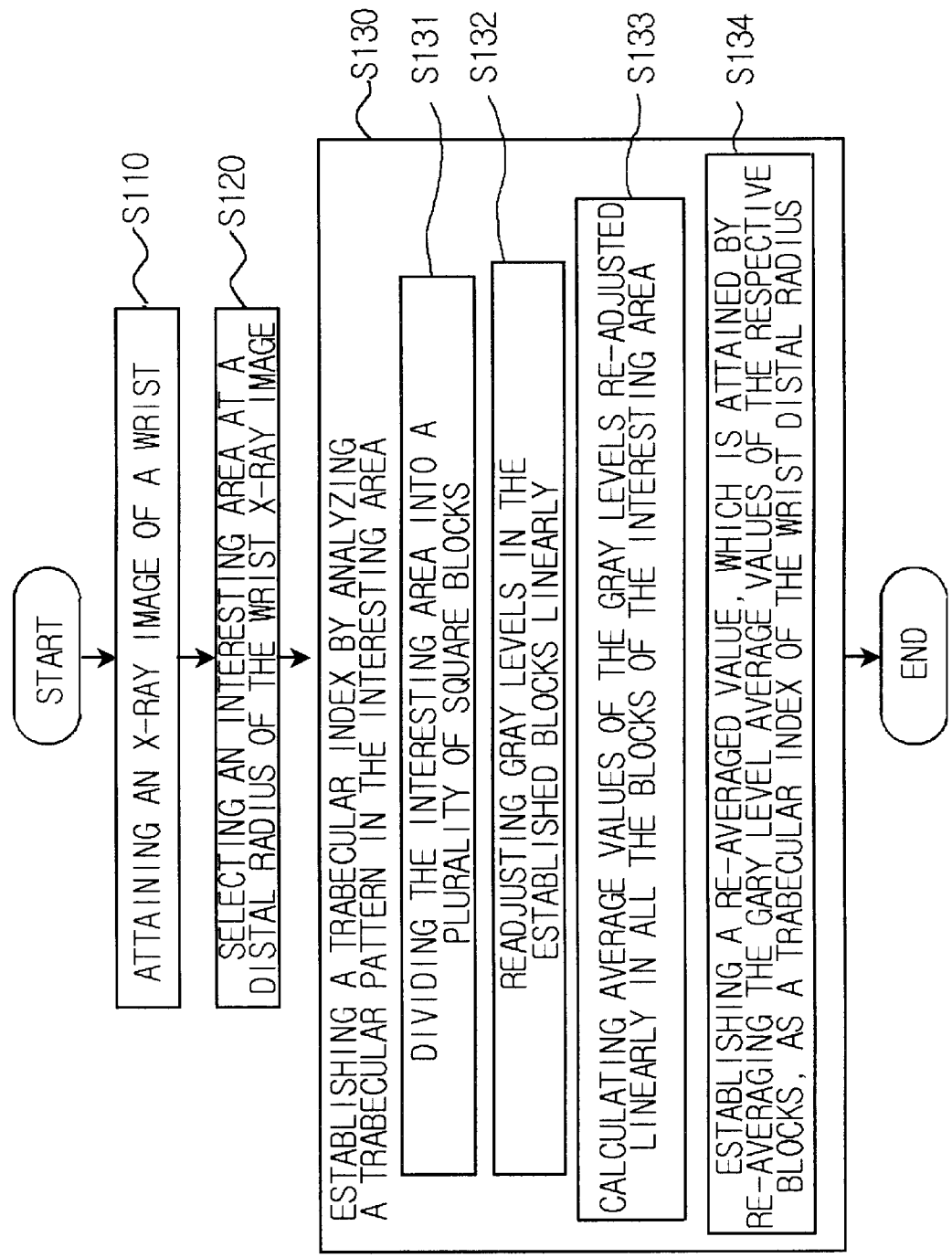
FIG. 1 shows a flow chart of establishing a trabecular index with a trabecular pattern on a simple x-ray image.
Figure 2:
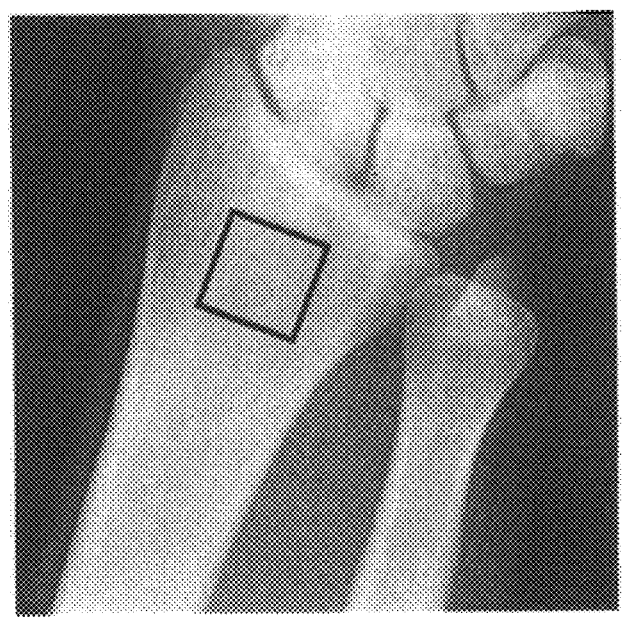
FIG. 2 shows a wrist x-ray image and a region of interest selected on the distal radius part of the wrist x-ray image.

FIG. 1 shows a flow chart of establishing a trabecular index with a trabecular pattern on a simple x-ray image. FIG. 2 shows a wrist x-ray image and a region of interest selected on the distal radius part of the wrist x-ray image.

Referring to FIG. 1, when establishing a trabecular index with a trabecular pattern on a simple x-ray image, an x-ray image of a bone, of which the trabecular index will be calculated, is prepared by x-ray radiography (S110). An x-ray image of a wrist is illustrated in FIG. 2.

The brightness of the wrist x-ray image is related to the quantity of x-rays absorbed per unit area. But, the brightness includes the x-ray absorption effect due to soft tissue, thereby generating a value which is quite different from the real bone mineral density. Therefore, the brightness information on the x-ray image may not be directly used for measuring bone mineral density.

Hence, it is necessary to establish a trabecular index by quantifying the trabecular pattern change appearing on the x-ray image and to use the trabecular index for the bone mineral density measurement. In order to quantify the trabecular pattern change appearing on an x-ray image due to the quantity decrease of a trabecular bone, a region of interest is selected on the distal radius of the wrist x-ray image (S120). An example of a square region of interest selected on the distal radius of the wrist x-ray image is illustrated in FIG. 2.

In accordance with the analysis of the trabecular pattern change within the region of interest, a trabecular index is established by quantifying the trabecular pattern change on the distal radius of the wrist x-ray image due to the decrease in trabecular bone quantity (S130).

Looking into the process of establishing a trabecular index of the region of interest, more specifically, the region of interest is divided into a plurality of square blocks (S131).

A length of a side of the square corresponds to an average interval of major trabecular lines appearing on the x-ray image. A simple x-ray image includes the effect due to soft tissue around the bone. Therefore, gray levels in the established blocks are readjusted linearly, wherein a minimum gray level becomes 0 and a maximum gray level becomes 255 (S132).

In this case, the effects due to the soft tissue, the x-ray radiographing condition, and the film developing condition, etc., are substantially reduced by establishing a plurality of blocks in the region of interest and by re-adjusting gray levels in the respective blocks.

Then, in each block of the region of interest, an average value over the linearly re-adjusted gray levels is calculated (S133).

Besides, a re-averaged value, which is attained by re-averaging the gray level average values of the respective blocks, is established as a trabecular index of the distal radius (S134).

Figure 3:
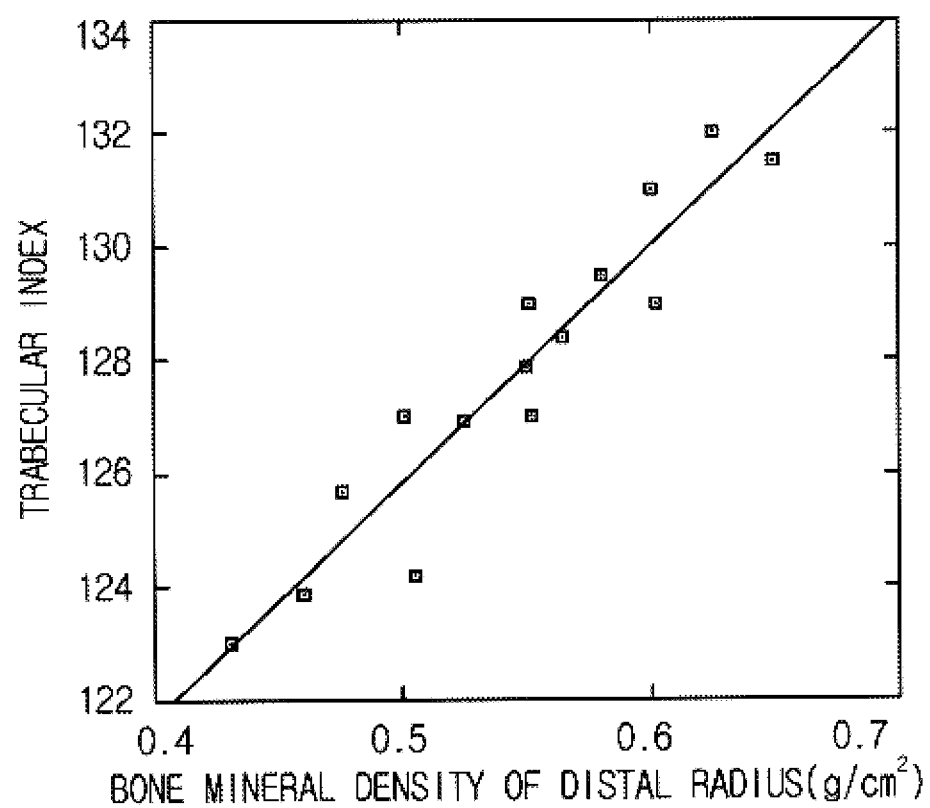
FIG. 3 shows a graph illustrating a relationship between a trabecular index and a quantitative bone mineral density.

FIG. 3 shows a graph of a relationship between a measured value of bone mineral density and a trabecular index in a distal radius.

Referring to FIG. 3, a real bone mineral density of a distal radius is strongly correlated to a trabecular index of the distal radius. Using this strong relationship, the bone mineral density of the distal radius is measured indirectly by the trabecular index of the distal radius.

A method for calibrating a trabecular index with a sawtooth-shaped rack, according to an embodiment of the present invention, will be explained in the following description by referring to FIGS. 4–7.

Figure 4:
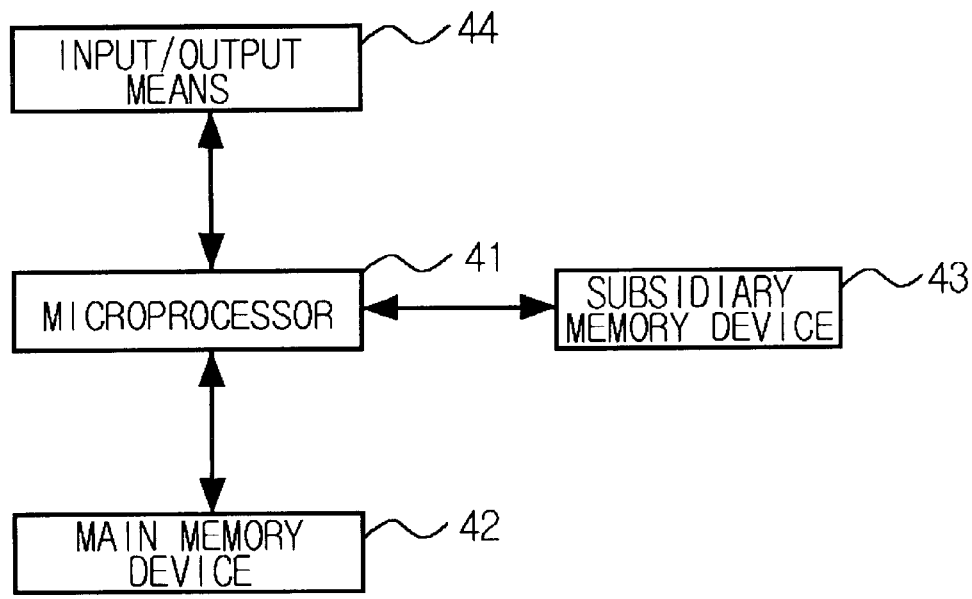
FIG. 4 shows a structural block diagram of a trabecular index calibrating apparatus according to an embodiment of the present invention.

FIG. 4 shows a structural block diagram of a hardware system realizing a trabecular index calibrating apparatus according to an embodiment of the present invention.

Referring to FIG. 4, a hardware system applied to the present invention consists of an input/output means 44 inputting/outputting data to/from an external user, a main memory device 42 and a subsidiary memory device 43 storing data required during calculating a trabecular index with a trabecular pattern of an x-ray image, and a microprocessor 41 executing an algorithm for controlling the main/subsidiary memory devices 42 and 43 and the input/output means 44, calculating a trabecular index with a trabecular pattern of an x-ray image, and calibrating the calculated trabecular index.

Figure 5:
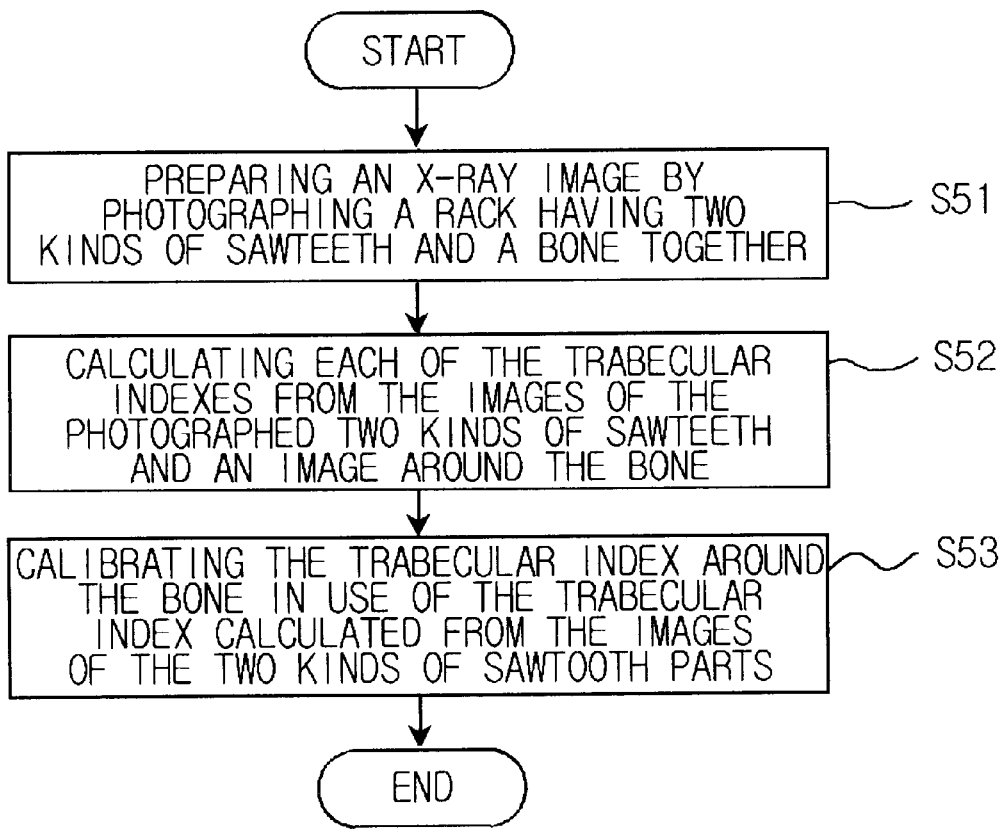
FIG. 5 shows a flow chart of a trabecular index calibrating method with a sawtooth-shaped rack according to an embodiment of the present invention.

An algorithm for calibrating a trabecular index is executed by the above system. And, a program including the process in FIG. 5 is installed in the microprocessor 41. In this case, once the algorithm for calibrating the trabecular index is executed, the program loads a simple x-ray image attained by radiographing a bone and a sawtooth-shaped rack together, calculates a trabecular index of the bone appearing on the x-ray image and calibrates the trabecular index of the bone by referring to the trabecular index calculated with respect to the sawtooth-shaped rack.

A specific operation of the calibrating method of the trabecular index will be explained in the following description by referring to FIGS. 5–7.

FIG. 5 shows a flow chart of a trabecular index calibrating method with a sawtooth-shaped rack according to an embodiment of the present invention. FIG. 6 shows the sawtooth-shaped rack used in the present invention. FIG. 7 shows an x-ray image obtained by radiographing a wrist and a sawtooth-shaped rack together according to the present invention.

Figure 6:
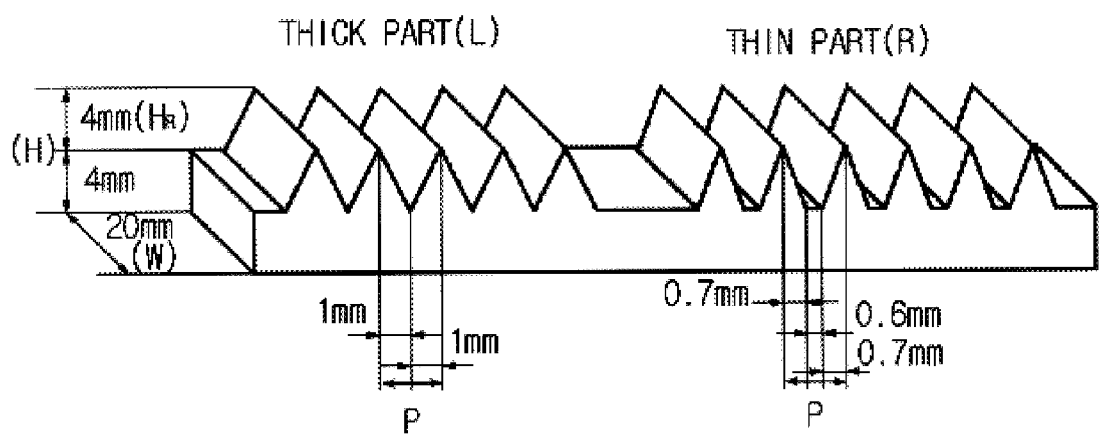
FIG. 6 shows a sawtooth-shaped rack used in the present invention.
Figure 7:
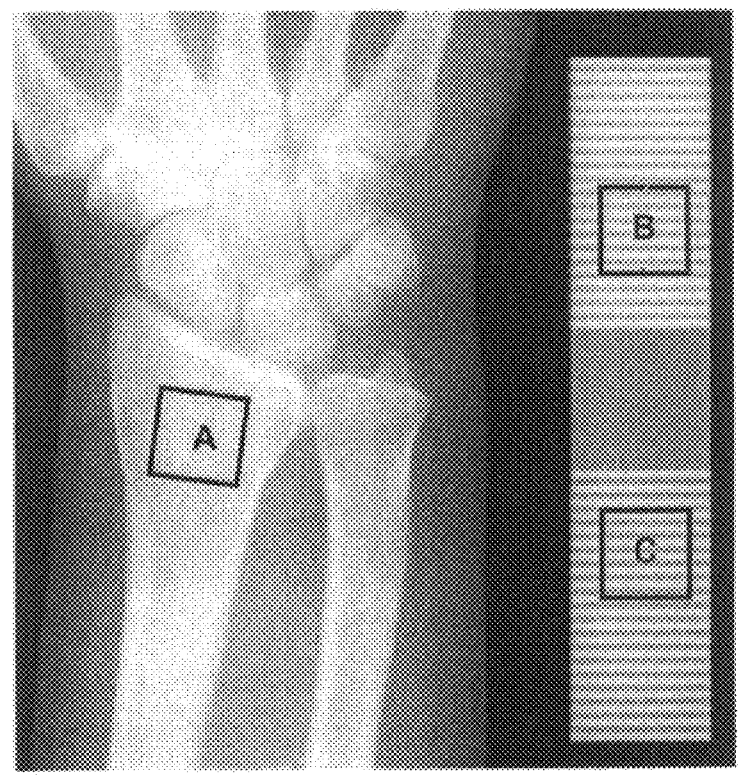
FIG. 7 shows an x-ray image obtained by radiographing a wrist and a sawtooth-shaped rack together according to the present invention.

Referring to FIG. 6, a rack having two kinds of sawteeth is used with the present invention. A width W of the rack bottom is 20 mm, a total height H of the rack is 8 mm, a height $H_R$ of a sawtooth of the rack is 4 mm, and each of the pitches P of the sawteeth is 2 mm both in the thick part L and in the thin part R. The thickness under the thick sawteeth L is 2 mm the same as that of the pitch P of the sawteeth. A plane of 0.6 mm wide is formed beneath the thin sawteeth R. Thus, the thickness beneath the sawteeth R is 1.4 mm.

Two kinds of sawteeth are used in the present invention. The sawteeth in the thick part L model themselves upon thick trabecular bone inside the bone, while the other sawteeth in the thin part R model themselves upon the fact that the bone quantity of the trabecular bone is reduced greatly. Therefore, two kinds of sawteeth provide standard models of showing that the trabecular bone is developed well or reduced greatly, respectively.

Using the rack with two kinds of sawteeth, a process of calibrating the trabecular index of the bone will be explained in the following description by referring to FIG. 5 and FIG. 7.

Referring to FIG. 5, an x-ray image is prepared (S51) by radiographing a rack having two kinds of sawteeth and a bone together. In the x-ray image, the sawteeth of the thick part (L in FIG. 6) are represented by a thick line which is the same as part B in FIG. 7, while the other sawteeth of the thin part (R in FIG. 6) are represented by a thin line which is the same as part C in FIG. 7.

Then, each of the trabecular indexes is calculated from the images (B and C in FIG. 7) of the two kinds of sawteeth and the image A of the bone (S52). The trabecular index of the bone is calibrated with the trabecular index calculated from the images of the two kinds of sawtooth parts (S53). Namely, an error in the trabecular index of the bone is calibrated by using the trabecular indexes of the sawtooth part of the x-ray images since the three images are radiographed under the same condition (an x-ray radiographing or an x-ray image inputting means) and the ideal trabecular indexes of the two kinds of sawteeth are fixed.

Specifically, it is assumed that the trabecular index value calculated from the image (B in FIG. 7) of the sawteeth in the thick part, the other trabecular index value calculated from the image (C in FIG. 7) of the sawteeth in the thin part, and another trabecular index value calculated from the bone image are "b", "c", and "a", respectively. Then, "b" and "c" are calibrated into ideal reference trabecular index values of "bb" and "cc", respectively, wherein "bb" is greater than "cc".

The trabecular index value "a" of the bone may be calibrated as in Equation 1 with the reference trabecular index values "bb" and "cc".

$$aa=(a-c)(bb-cc)/(b-c)+cc,$$

wherein "aa" is a calibrated trabecular index value of the bone.

As mentioned in the above descriptions, preferred embodiment of the present invention are provided. But, the numerical values and images used in the present invention may be modified for improving the performance of the present invention.

When a trabecular index is to be calculated by analyzing a trabecular pattern appearing on a simple x-ray image, the present invention calibrates an error of the trabecular index due to the x-ray image radiographing conditions and/or the characteristics of the image input devices. In order to achieve the object of the present invention, an x-ray image is attained by radiographing a bone and a sawtooth-shaped rack together, a trabecular index of the bone appearing on the x-ray image is calculated, and the trabecular index of the bone is calibrated by referring to the trabecular index calculated at the sawtooth-shaped rack.

Accordingly, the present invention eliminates an error of a bone trabecular index due to the x-ray image radiographing conditions and/or the characteristics of the image input devices attaining an x-ray image of a bone and a sawtooth-shaped rack together, by calculating a trabecular index of the bone appearing on the x-ray image, and by calibrating the trabecular index of the bone with the trabecular index calculated with respect to the sawtooth-shaped rack.

Moreover, the present invention improves the precision of measuring bone mineral density by calculating a trabecular index by quantifying a trabecular pattern change appearing on an x-ray image due to the change of bone mineral density, and by calibrating an error of the trabecular index.

It will be apparent to those skilled in the art that various modifications and variations can be made in this method for calibrating a trabecular index with a sawtooth-shaped rack of the present invention, without departing from the spirit or scope of the invention. Thus, it is intended that the present invention cover the modifications and variations of this invention provided they come within the scope of the appended claims and equivalents.

What we claim:

1. A method for calibrating a trabecular index with a sawtooth-shaped rack, wherein bone mineral density is measured with a trabecular index calculated from an x-ray image and an error of the trabecular index is calibrated by a method of calibrating a trabecular index, comprising the steps of:

a first step of preparing the x-ray image by radiographing a bone and the sawtooth-shaped rack together;

a second step of attaining trabecular indexes from the x-ray image of the rack and the bone; and a third step of calibrating the trabecular index of the bone with the trabecular index of the rack.

2. The method for calibrating a trabecular index with a sawtooth-shaped rack according to claim 1, wherein the sawtooth-shaped rack consists of a thick sawtooth part modeled upon a figure of high bone mineral density owing to thick trabecular bone inside the bone and a thin sawtooth part modeled upon the fact that bone quantity of the trabecular bone is greatly reduced.

3. The method for calibrating a trabecular index with a sawtooth-shaped rack according to claim 2, wherein the sawteeth of the thick and thin sawtooth parts have a same pitch length and a same height, and wherein a thickness under the sawteeth of the thick sawtooth part is thicker than a thickness under the sawteeth of the thin sawtooth part.

4. The method for calibrating a trabecular index with a sawtooth-shaped rack according to claim 2 or claim 3, wherein the calibrated trabecular index value of the bone is attained by a formula provided below, wherein a trabecular index value of the bone is "a," a trabecular index value of the thick sawtooth part is "b," a trabecular index value of the thin sawtooth part is "c," and ideal reference trabecular index values of the sawteeth are "bb" and "cc," respectively:

$$aa=(a-c)(bb-cc)/(b-c)+cc.$$

5. A recording means for storing a program to realize a method for calibrating a trabecular index, the program comprising:

a first step of preparing an x-ray image by radiographing a bone and a sawtooth-shaped rack together;

a second step of attaining trabecular indexes from the x-ray image of the rack and the bone; and a third step of calibrating the trabecular index of the bone with the trabecular index of the rack.

* * * * *